(12) United States Patent
Boomer et al.

(10) Patent No.: US 10,722,275 B2
(45) Date of Patent: *Jul. 28, 2020

(54) ADJUSTABLE-ANGLE SPINAL FIXATION ELEMENT

(71) Applicant: Medos International Sàrl, Le Locle (CH)

(72) Inventors: Mark C. Boomer, Phoenix, AZ (US); Raymond F. Murphy, Attleboro, MA (US); Bryan S. Jones, West Roxbury, MA (US)

(73) Assignee: Medos International Sàrl, Le Locle (CH)

( * ) Notice: Subject to any disclaimer, the term of this patent is extended or adjusted under 35 U.S.C. 154(b) by 58 days.

This patent is subject to a terminal disclaimer.

(21) Appl. No.: 15/959,855

(22) Filed: Apr. 23, 2018

(65) Prior Publication Data
US 2018/0235668 A1 Aug. 23, 2018

Related U.S. Application Data

(63) Continuation of application No. 15/299,002, filed on Oct. 20, 2016, now Pat. No. 9,974,572, which is a
(Continued)

(51) Int. Cl.
*A61B 17/70* (2006.01)

(52) U.S. Cl.
CPC ...... *A61B 17/7052* (2013.01); *A61B 17/7002* (2013.01); *A61B 17/705* (2013.01);
(Continued)

(58) Field of Classification Search
CPC ............ A61B 17/7023; A61B 17/7002; A61B 17/7013; A61B 17/705; A61B 17/7052; A61B 17/7055; A61B 17/7059
(Continued)

(56) References Cited

U.S. PATENT DOCUMENTS

| 1,365,532 | A | 1/1921 | Mountain |
| 2,077,844 | A | 4/1937 | Wycliffe |

(Continued)

FOREIGN PATENT DOCUMENTS

| EP | 0 953 316 A1 | 11/1999 |
| FR | 2781359 A1 | 1/2000 |

(Continued)

OTHER PUBLICATIONS

[No Author Listed] Oasys Occipito-Cervico-Thoracic System, Stryker Brocher. Date unknown.
(Continued)

*Primary Examiner* — Pedro Philogene
*Assistant Examiner* — David C Comstock
(74) *Attorney, Agent, or Firm* — Nutter McClennen & Fish LLP

(57) ABSTRACT

A spinal fixation device is provided having first and second elongate members that are angularly adjustable relative to one another. Each elongate member can include a connecting feature formed on a terminal end thereof, and each connecting feature can be coupled to one another to allow angular movement of the first and second elongate members. The device can also include a locking mechanism that is adapted to couple to the connecting feature on each of the first and second elongate members to lock the elongate members in a fixed position relative to one another.

22 Claims, 13 Drawing Sheets

Related U.S. Application Data continuation of application No. 14/755,497, filed on Jun. 30, 2015, now Pat. No. 9,498,258, which is a continuation of application No. 14/317,034, filed on Jun. 27, 2014, now Pat. No. 9,155,565, which is a continuation of application No. 12/985,000, filed on Jan. 5, 2011, now Pat. No. 8,795,339, which is a continuation of application No. 10/708,919, filed on Mar. 31, 2004, now Pat. No. 7,909,852.

(52) U.S. Cl.
CPC ...... *A61B 17/7013* (2013.01); *A61B 17/7023* (2013.01); *A61B 17/7059* (2013.01); *A61B 17/7055* (2013.01)

(58) Field of Classification Search
USPC ....... 606/246, 250, 251, 253, 256, 257, 259, 606/260, 261, 264, 265, 278, 279; 623/18.11, 20.12, 20.14, 20.21, 20.24, 623/20.28, 20.36, 21.15, 23.39, 23.44, 623/23.47; 403/71, 79, 156, 157, 235
See application file for complete search history.

(56) References Cited

U.S. PATENT DOCUMENTS

| | | | |
|---|---|---|---|
| 3,342,922 A | 9/1967 | Karpovich et al. | |
| 3,385,615 A | 5/1968 | Hussey | |
| 3,816,854 A | 6/1974 | Schlein | |
| 4,433,677 A | 2/1984 | Ulrich et al. | |
| 5,405,347 A | 4/1995 | Lee et al. | |
| 5,509,328 A | 4/1996 | Lai et al. | |
| 5,549,607 A * | 8/1996 | Olson | A61B 17/7037 606/250 |
| 5,643,263 A | 7/1997 | Simonson | |
| 5,645,544 A | 7/1997 | Tai et al. | |
| 5,662,651 A * | 9/1997 | Tornier | A61B 17/7002 606/278 |
| 5,662,653 A | 9/1997 | Songer et al. | |
| 5,676,665 A * | 10/1997 | Bryan | A61B 17/7032 606/250 |
| 5,885,285 A | 3/1999 | Simonson | |
| 5,947,967 A | 9/1999 | Barker | |
| 5,984,923 A | 11/1999 | Breard | |
| 6,007,536 A | 12/1999 | Yue | |
| 6,183,473 B1 | 2/2001 | Ashman | |
| 6,238,396 B1 | 5/2001 | Lombardo | |
| 6,284,014 B1 | 9/2001 | Carden | |
| 6,296,644 B1 | 10/2001 | Saurat et al. | |
| 6,402,749 B1 | 6/2002 | Ashman | |
| 6,471,703 B1 | 10/2002 | Ashman | |
| 6,551,318 B1 | 4/2003 | Stahurski | |
| 6,562,038 B1 | 5/2003 | Morrison | |
| 6,579,292 B2 | 6/2003 | Taylor | |
| 6,648,887 B2 | 7/2003 | Ashman | |
| 6,620,164 B2 | 9/2003 | Ueyama et al. | |
| 6,626,906 B1 | 9/2003 | Young | |
| 6,652,527 B2 | 11/2003 | Zucherman et al. | |
| 6,663,632 B1 | 12/2003 | Frigg | |
| 6,685,705 B1 | 2/2004 | Taylor | |
| 6,689,133 B2 | 2/2004 | Morrison et al. | |
| 6,832,999 B2 | 12/2004 | Ueyama et al. | |
| 6,872,209 B2 | 3/2005 | Morrison | |
| 7,473,269 B1 | 1/2009 | Hynes | |
| 7,517,359 B2 | 4/2009 | Drewry et al. | |
| 7,909,852 B2 | 3/2011 | Boomer et al. | |
| 8,109,974 B2 | 2/2012 | Boomer et al. | |
| 8,795,339 B2 | 8/2014 | Boomer et al. | |
| 8,870,918 B2 | 10/2014 | Boomer et al. | |
| 9,155,565 B2 | 10/2015 | Boomer et al. | |
| 9,498,258 B2 | 11/2016 | Boomer et al. | |
| 9,974,572 B2 | 5/2018 | Boomer et al. | |
| 2002/0049446 A1* | 4/2002 | Harkey, III | A61B 17/7044 606/70 |
| 2002/0138077 A1 | 9/2002 | Ferree | |
| 2002/0193794 A1 | 12/2002 | Taylor | |
| 2003/0171751 A1 | 9/2003 | Ritland | |
| 2003/0176863 A1 | 9/2003 | Ueyama et al. | |
| 2003/0176864 A1 | 9/2003 | Ueyama et al. | |
| 2003/0191473 A1 | 10/2003 | Taylor | |
| 2004/0002708 A1 | 1/2004 | Ritland | |
| 2004/0015166 A1 | 1/2004 | Gorek | |
| 2004/0039384 A1 | 2/2004 | Boehm et al. | |
| 2004/0133203 A1 | 7/2004 | Young et al. | |
| 2004/0210216 A1* | 10/2004 | Farris | A61B 17/7038 606/264 |
| 2005/0113835 A1 | 5/2005 | Ashman | |
| 2005/0228376 A1 | 10/2005 | Boomer et al. | |
| 2008/0033434 A1 | 2/2008 | Boomer et al. | |
| 2011/0098748 A1 | 4/2011 | Jangra | |
| 2011/0098749 A1 | 4/2011 | Boomer et al. | |
| 2011/0245874 A1 | 10/2011 | Boomer et al. | |
| 2014/0309696 A1 | 10/2014 | Boomer et al. | |
| 2015/0305778 A1 | 10/2015 | Boomer et al. | |
| 2017/0035464 A1 | 2/2017 | Boomer et al. | |

FOREIGN PATENT DOCUMENTS

| | | |
|---|---|---|
| JP | 2003-250807 A | 9/2003 |
| WO | 02/34150 A2 | 5/2002 |
| WO | 02/76315 A1 | 10/2002 |
| WO | 2005/041799 A1 | 5/2005 |

OTHER PUBLICATIONS

[No Author Listed] Summit SI OCT Spinal Fixation System, DePuy AcroMed Brochure (May 2003).

Currier, Bradford L., "Surgical Technique" "Summit Occipito-Cervico-Thoracic Spinal Fixation System" pp. 1-25 (2003), DePuy AcroMed Brochure.

European Search Report dated Jan. 27, 2010, for EP Application No. EP09180080.

European Examination Report, dated Sep. 15, 2010, for EP Application No. EP09180080.

International Search Report dated Jul. 13, 2005 for PCT/US05/04028—(3 pgs).

International Search Report dated Nov. 23, 2007—(PCT/US05/34689, 15 pgs).

U.S. Appl. No. 10/708,919, filed Mar. 31, 2004, Adjustable-Angle Spinal Fixation Element.

U.S. Appl. No. 11/873,847, filed Oct. 17, 1007, Adjustable-Angle Spinal Fixation Element.

U.S. Appl. No. 12/985,000, filed Jan. 5, 2011, Adjustable-Angle Spinal Fixation Element.

U.S. Appl. No. 13/159,154, filed Jun. 13, 2011, Adjustable-Angle Spinal Fixation Element.

U.S. Appl. No. 14/317,034, filed Jun. 27, 2014, Adjustable-Angle Spinal Fixation Element.

U.S. Appl. No. 14/755,497, filed Jun. 30, 2015, Adjustable-Angle Spinal Fixation Element.

U.S. Appl. No. 15/299,002, filed Oct. 20, 2016, Adjustable-Angle Spinal Fixation Element.

* cited by examiner

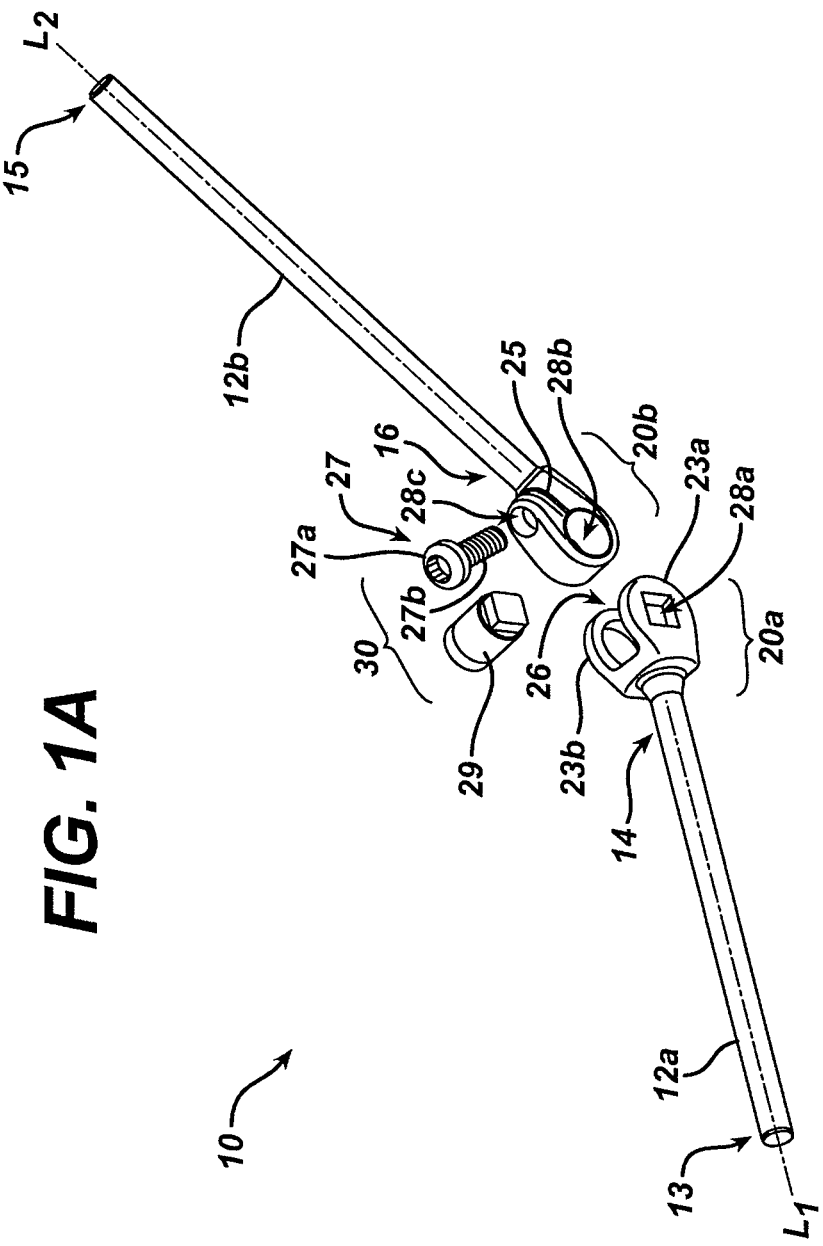

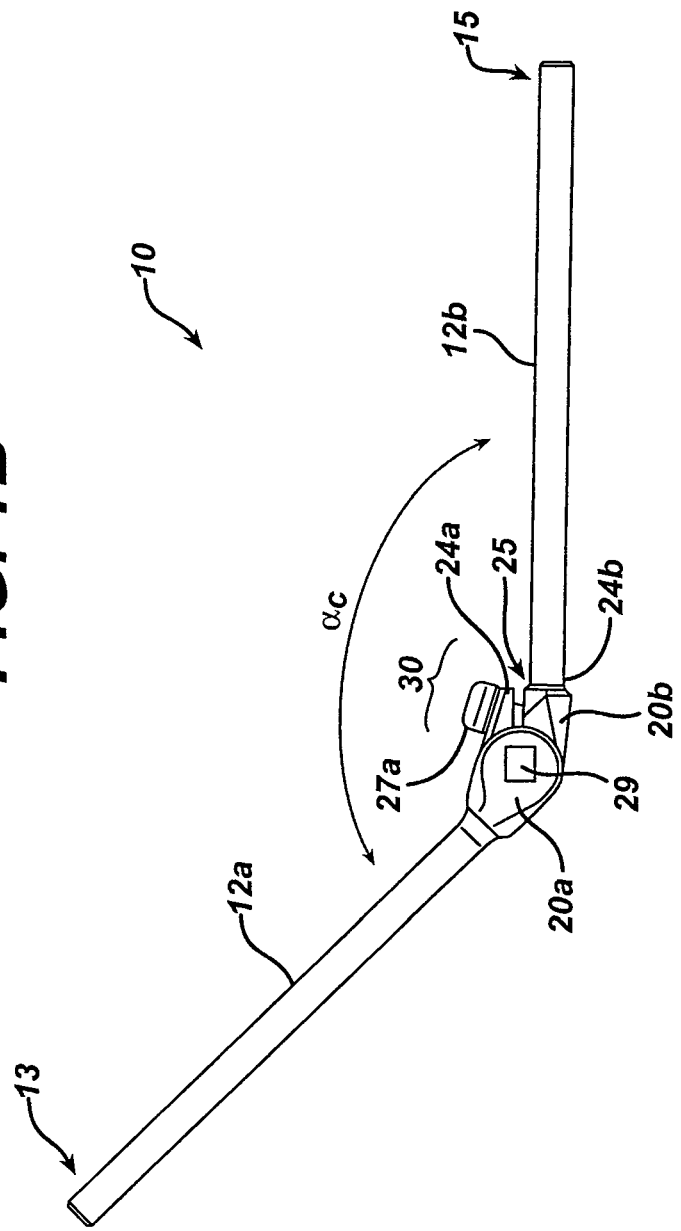

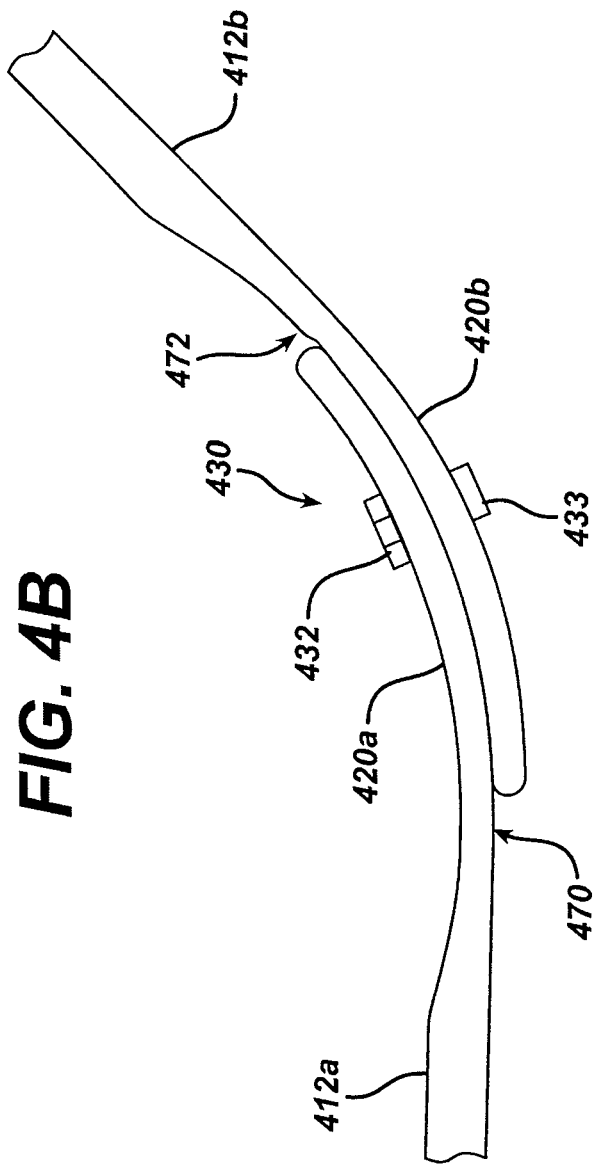

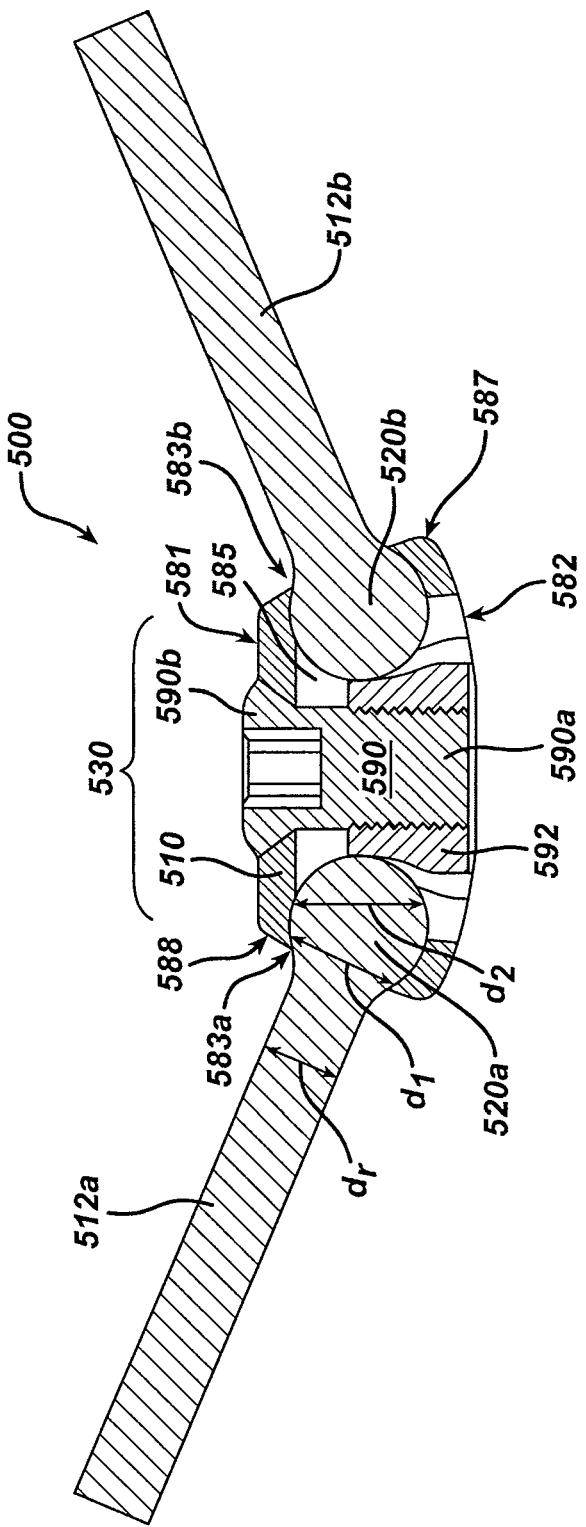

ADJUSTABLE-ANGLE SPINAL FIXATION ELEMENT

CROSS-REFERENCE TO RELATED APPLICATIONS

This application is a continuation of U.S. patent application Ser. No. 15/299,002, filed on Oct. 20, 2016, and entitled "Adjustable-Angle Spinal Fixation Element." U.S. patent application Ser. No. 15/299,002 is a continuation of U.S. patent application Ser. No. 14/755,497, filed on Jun. 30, 2015, entitled "Adjustable-Angle Spinal Fixation Element," and now issued as U.S. Pat. No. 9,498,258. U.S. patent application Ser. No. 14/755,497 is a continuation of U.S. patent application Ser. No. 14/317,034, filed on Jun. 27, 2014, entitled "Adjustable-Angle Spinal Fixation Element," and now issued as U.S. Pat. No. 9,155,565. U.S. patent application Ser. No. 14/317,034 is a continuation of U.S. patent application Ser. No. 12/985,000, filed on Jan. 5, 2011, entitled "Adjustable-Angle Spinal Fixation Element," and now issued as U.S. Pat. No. 8,795,339. U.S. patent application Ser. No. 12/985,000 is a continuation of U.S. patent application Ser. No. 10/708,919, filed on Mar. 31, 2004, entitled "Adjustable-Angle Spinal Fixation Element," and now issued as U.S. Pat. No. 7,909,852. Each of these applications is hereby incorporated by reference in its entirety.

FIELD OF THE INVENTION

The present application relates to devices for use in spinal surgery, and in particular to spinal fixation devices having an adjustable angle.

BACKGROUND OF THE INVENTION

Stabilization of the spine is often required following trauma, tumor, or degenerative pathologies. Although each region of the spine presents unique clinical challenges, posterior fixation of the cervical spine is particularly challenging. The anatomy of the cervical spine makes it a technically challenging area to instrument. Specifically, several vital neural and vascular structures, including the vertebral arteries, nerve roots, and spinal cord, must be avoided during surgery.

Current methods of posterior cervical stabilization include the use of an occipital spinal plate and a transition rod for fixation of the cervico-thoracic junction. Such devices typically include a spinal fixation element, such as a relatively rigid fixation rod, that is coupled to adjacent vertebrae by attaching the element to various anchoring devices, such as hooks, bolts, wires, or screws. Often two rods are disposed on opposite sides of the spinous process in a substantially parallel relationship. The fixation rods can have a predetermined contour that has been designed according to the properties of the target implantation site, and once installed, the rods hold the vertebrae in a desired spatial relationship, either until healing or spinal fusion has taken place, or for some longer period of time.

It is often the case that the predetermined contour of a fixation rod does not exactly fit the contour of the implantation site. This may be attributed to various factors including a patients age, which directly relates to the size of their spinous process, irregular contouring due to disease or injury, or malformation due to a birth defect. These conditions often make it impossible to use a pre-contoured fixation rod. In these cases, multiple rods projecting at multiple angles are used, however such devices can complicate the surgery, as well as the recovery, and they can add undue strain on the spinous process, possibly resulting in an unsuccessful repair of the spine.

Accordingly, there presently exists a need for improved spinal fixation devices that can be easily installed and that allow for angular adjustment and subsequent locking. There is also a need for spinal fixation devices that have a low-profile to avoid potential irritation and injury to the patient.

SUMMARY OF THE INVENTION

The present invention generally provides a spinal fixation device having first and second elongate members that are angularly adjustable relative to one another. Each elongate member can include a connecting feature formed on a terminal end thereof, and each connecting feature can be coupled to one another to allow angular movement of the first and second elongate members. The device can also include a locking mechanism that is adapted to couple to the connecting feature on each of the first and second elongate members to lock the elongate members in a fixed position relative to one another.

In one embodiment, the connecting feature on the first elongate member is a female connector, and the connecting feature on the second elongate member is a male connector that is adapted to receive the female connector. The female connector preferably includes opposed arms defining a recess therebetween for receiving the male connector. A bore can extend through the opposed arms on the female connector and through the male connector for receiving a central mating element that is adapted to mate the male and female connectors to one another. In an exemplary embodiment, the central mating element is a cylindrical member that is adapted to allow at least one of the first and second elongate members to rotate thereabout. More preferably, however, the cylindrical member is fixedly coupled to a portion of the female connector, and the male connector is free to rotate about the cylindrical member.

In use, the locking mechanism can engage the cylindrical member to prevent movement of the male connector relative to the female connector. While a variety of locking mechanisms can be used, in one embodiment the locking mechanism can be in the form of a slot extending through the male connector such that the male connector is in the form of a clamp, and the locking mechanism can also include a fastening element that is adapted to engage the male connector to clamp the cylindrical member within the bore. The fastening element is preferably a threaded member.

In other aspects of the present invention, the connecting feature on each of the first and second elongate members can rotate about a central axis extending substantially perpendicular to an axis of each first and second elongate members. More preferably, each connecting feature can include opposed inner and outer surfaces, and the inner surface on each connecting feature can be in contact one another. In an exemplary embodiment, the inner surface on each connecting feature is adapted to prevent rotation of the first and second elongate members relative to one another when the locking mechanism is in a locked configuration. The connecting features can also optionally include anti-rotation features, such as gear teeth, formed on the inner surface of each connecting feature.

In further aspects, a first bore can extend through the inner and outer surface of the connecting feature on the first elongate member and a second bore extending through the inner and outer surface of the connecting feature on the second elongate member. In one embodiment, the bores can be adapted to receiving the locking mechanism, which can be, for example, a fastening element having a head and a shaft with threads formed thereon. The first bore is preferably non-threaded for freely rotatably receiving a portion of the shaft of the fastening element, and the second bore is preferably threaded for mating with the threads formed on the shaft of the locking mechanism.

In an alternative embodiment, a pin member can be disposed through the first and second bores extending through the inner and outer surfaces of the connecting feature, and the pin member can include a transverse bore extending therethrough for receiving at least a portion of the locking mechanism. A receiving bore can be formed in at least one connecting feature, and the receiving bore can be in communication with the central bore to allow the locking mechanism to extend therethrough and into the transverse bore in the pin member. In a further embodiment, the locking mechanism can be adapted to engage the pin member to translate the first and second connecting features toward one another to lock the first and second elongate members in a fixed position relative to one another.

In yet another embodiment of the present invention, the connecting feature on each of the first and second elongate members can be slidably coupled to one another. More preferably, the connecting feature on each of the first and second elongate members is a substantially curved terminal portion, and the terminal portion are complementary for slidably mating to one another. Each terminal portion can include a slot formed therein for receiving the locking mechanism. Each terminal portion can also include one or more anti-sliding surface features formed on a portion thereof to prevent movement of the first and second elongate members relative to one another when the locking mechanism is in a locked configuration.

BRIEF DESCRIPTION OF THE DRAWINGS

The invention will be more fully understood from the following detailed description taken in conjunction with the accompanying drawings, in which:

FIG. 1A is an exploded view of one embodiment of an adjustable-angle spinal fixation device having male and female connecting features according to the present invention;

FIG. 1B is a side, assembled view of the adjustable-angle spinal fixation device shown in FIG. 1A in a locked position;

FIG. 4B is a side view of the adjustable-angle spinal fixation device shown in FIG. 4A in a locked position;

FIG. 5A is a side view of another embodiment of an adjustable-angle spinal fixation device according to the present invention having a locking mechanism that provides a polyaxial connection with first and second spinal fixation elements coupled thereto;

DETAILED DESCRIPTION OF THE INVENTION

Figure 1C:
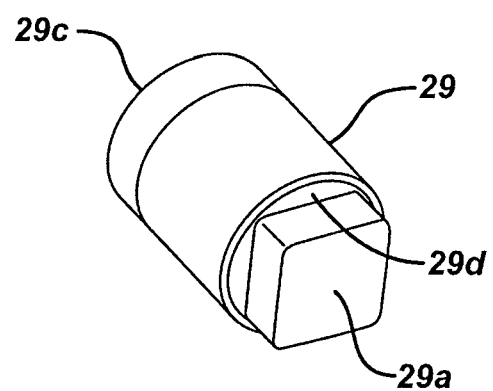
FIG. 1C is a perspective view of a central mating element of the adjustable-angle spinal fixation device shown in FIG. 1A.

The present invention provides various angularly-adjustable spinal fixation devices, each of which generally includes first and second elongate members 12a, 12b, a connecting feature 20 formed on a terminal end of each of the first and second elongate members 12a, 12b, and a locking mechanism 30 that is adapted to lock the first and second elongate members 12a, 12b in a fixed position relative to one another. The elongate members 12a, 12b are preferably spinal rods and/or plates that are used, for example, in the stabilization of the spine following trauma, tumor, or degenerative pathologies. Among many other advantages, the devices are particularly useful to allow a spinal rod to be positioned and locked in a desired angular orientation without the need to reshape the rod, and without requiring the point of adjustment to be attached to the spine of a patient.

FIGS. 1A-1B illustrate one exemplary embodiment of a spinal fixation device 10 having first and second elongate members 12a, 12b, a connecting feature 20a, 20b formed on a terminal end 14, 16 of each of the first and second elongate members 12a, 12b, and a locking mechanism 30 that is adapted to lock the first and second elongate members 12a, 12b in a fixed position relative to one another. In use, the first and second elongate members 12a, 12b can be angularly adjusted relative to one another and, once properly positioned, they can be locked in a fixed position relative to one another using the locking mechanism 30.

The first and second elongate members 12a, 12b can each have any shape or size, and each elongate member 12a, 12b can vary in diameter relative to one another. The elongate members 12a, 12b can also vary in length depending on the intended use. In the illustrated embodiment, the first and second elongate members 12a, 12b are substantially cylindrical spinal rods, each having a terminal end 13, 15 that is adapted to mate to a spinal anchor, such as a hook, screw, bolt, plate, etc. The opposed terminal end 14, 16 of each elongate member 12a, 12b includes the connecting feature 20a, 20b formed thereon and mated to one another.

Figure 1D:
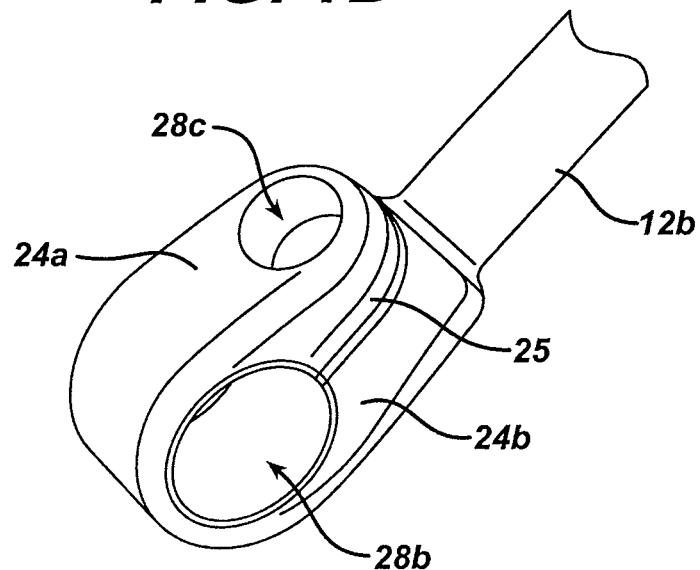
FIG. 1D is an enlarged perspective view of a male connector of the adjustable-angle spinal fixation device shown in FIG. 1A.
Figure 1E:
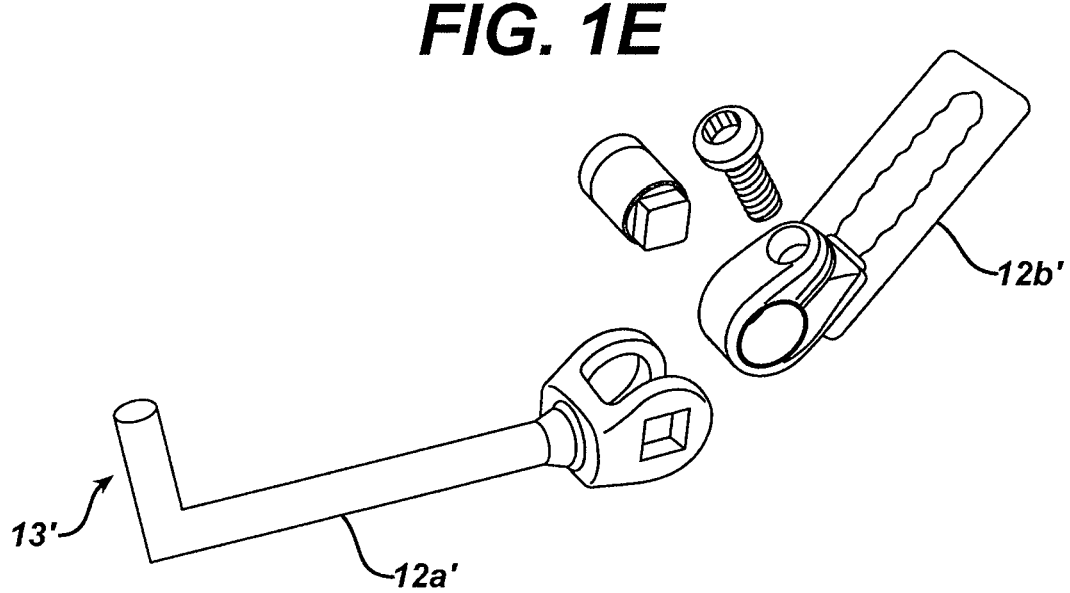
FIG. 1E is an exploded view of another embodiment of an adjustable-angle spinal fixation device having a spinal fixation plate with a male connecting feature and a spinal rod with a female connecting feature for mating to the male connecting feature.

While the terminal ends 13, 15 of the elongate members 12a, 12b shown in FIGS. 1A-1B extend along the axis of the elongate members 12a, 12b, the terminal ends 13, 15 can extend at an angle relative to the elongate members 12, 12b. For example, as shown in FIG. 1E, the terminal end 13' of one of the elongate members, e.g., the first elongate member 12a', can extend at a 90° angle relative to the longitudinal axis of the second elongate member 12b, as shown in FIG. 1E. In other embodiments, one or both of the elongate members can be in the form of a spinal fixation plate. For example, as shown in FIG. 1E, the second elongate member 12b is in the form of a spinal fixation plate 12b', rather than a spinal rod.

Continuing to refer to FIGS. 1A-1B, each connecting feature 20a, 20b can have a variety of configurations, but they should be adapted to allow for angular adjustability of the first and second elongate members 12a, 12b relative to one another. In the embodiment shown in FIGS. 1A-1B, the connecting feature 20a on the first elongate member 12a is in the form of a female connector, and the connecting feature 20b on the second elongate member 12 is in the form of a male connector. The terminal ends 14, 16 of the elongate members 12a, 12b can mate to the connectors 20a, 20b at any location, but in an exemplary embodiment the elongate members 12a, 12b are positioned such that the connectors 20a, 20b do not interfere with the patient's spinal anatomy.

While the male and female connectors 20a, 20b can have a variety of configurations, in an exemplary embodiment the female connector 20a has opposed arms 23a, 23b that are spaced a distance apart from one another to form an open recess 26 therebetween for seating the male connector 20b. Each arm 23a, 23b can vary in shape and size, but in an exemplary embodiment, as shown, the arms 23a, 23b each have a substantially circular shape. The male connector 20b can also vary in shape and size, but it preferably has a shape that corresponds to the female connector 22, and more preferably the male connector 20b is substantially circular.

Each connector member 20a, 20b also preferably includes a central bore 28a, 28b that extends therethrough in a direction that is substantially perpendicular to a longitudinal axis $L_1$, $L_2$ each of the first and second elongate members 12a, 12b. The central bore 28a, 28b is adapted to receive a central mating element 29 therethrough for mating the connectors 20a, 20b, and for allowing one or both connectors 20a, 20b to rotate thereabout. The central mating element 29 can have a variety of configurations, however FIG. 1C illustrates a central mating element 29 having a substantially cylindrical shape and including proximal and distal ends 29c, 29d. In a preferred embodiment, one of the connectors, e.g., the female connector 20a, is configured to receive the mating element 29 such that the female connector 20a and the mating element 29 are in a fixed position relative to one another, and the male connector 20b is free to rotate about the mating element 29 and relative to the female connector 20a. This can be achieved, for example, by providing complementary features on the mating element 29 and the female connector 20a to prevent rotation relative to one another. As shown in FIGS. 1A-1C, the portion of the bore 28a that extends through the first arm 23a has a substantially square shape, and the distal end 29d of the central mating element 29 includes a substantially square-shaped protrusion 29a formed thereon and adapted to be disposed within the corresponding bore 28a formed in the female connector 20a. As a result, when the device 10 is in use, the female connector 20a is locked in a fixed position relative to the mating element 29, but the male connector 20b is free to rotate thereabout. A person skilled in the art will appreciate that the complementary features on the mating element 29 and the female connector 20a can have a variety of other configurations and by way of non-limiting example, the complementary mating features can have a hexagonal shape, an octagonal shape, a D-shape, or any other shape that prevents rotation of the female connector 20a relative to the mating element 29. In other embodiments, the mating element 29 and the female connector 20a can be fixedly mated to one another, for example, by welding the components together, to prevent rotation of the female connector 20a relative to the mating element 29.

As previously stated, the device 10 also includes a locking mechanism 30 that is adapted to lock the first and second elongate members 12a, 12b in a fixed position relative to one another. While virtually any technique can be used to lock the elongate members 12a, 12b in a fixed position, FIGS. 1A, 1B, and 1D illustrate an exemplary embodiment of a locking mechanism 30. In this embodiment, the male connector 20b is in the form of a clamp mechanism and more particularly it includes a slot 25 extending therethrough and in communication with the central bore 28 formed therein, as shown in more detail in FIG. 1D.

The slot 25 separates the male connector 20b into upper and lower portions 24a, 24b that are movable between an open position and a closed position in which the male connector 20b is adapted to engage the mating element 29 extending through the central bore 28b.

In order to move the upper and lower portions 24a, 24b to the closed position, the male connector 24 can include a receiving bore 28c formed therein and extending through the upper and lower portions 24a, 24b. The receiving bore 28c is adapted to receive a fastening element 27 that is effective to pull one or both of the upper and lower portions 24a, 24b toward one another to close the slot 25. As a result, the central bore 28b extending through the male connector 20b is decreased in size, thereby allowing the male connector 20b to engage the mating element 29 and preventing rotation of the second elongate member 12b relative to the first elongate member 12a.

The fastening element 27 that is disposed through the receiving bore 28c can have a variety of configurations, and it can be, for example, a screw, anchor, or bolt. In the illustrated embodiment, as shown in FIG. 1A, the fastening element 27 is a threaded member, e.g., a screw, having a head 27a and a thread shank 27b. The receiving bore 28c formed in the male connector 20b can thus includes threads formed therein for mating with the threaded shank 27b on the fastening element 27. More preferably, however, the portion of the receiving bore 28c formed in the upper portion 24a of the male connector 20b is non-threaded to allow free rotation of the threaded member 27 with respect thereto, and the portion of the receiving bore 28c formed in the lower portion 24b of the male connector 20b is threaded to mate with the threaded shank 27b. This allows the fastening element 27 to pull the upper portion 24a toward the lower portion 24b, thereby locking the portions 24a, 24b relative to one another and locking the male connector 20b relative to the mating element 29.

Those skilled in the art will appreciate that the receiving bore 28b and male connector 20b can be a variety of other configurations to facilitate locking of the male connector 20b. By way of non-limiting example, the central mating element 29 and/or an inner surface of the bore 28b on the male connector 20b can have anti-rotation features formed thereon, such that when the male connector 20b is closed the anti-rotation features can assist in securing the male connector 20b around the central mating element 29. The anti-rotation features can be, for example, a non-slip coating applied to the surface of the mating element 29 and/or the bore 28b, teeth or knurling formed on the surface of the mating element 29 and/or the bore 28b, or other gripping features known to one skilled in the art.

In use, the fastening element 27 can be partially threaded into the bore 28c formed in the male connector 20b to allow the first and second elongate members 12a, 12b to rotate relative to one another. Although the elongate members 12a, 12b can be adapted for multi-axial rotation, in the illustrated embodiment the elongate members 12a, 12b rotate along a single plane. Each elongate member 12a, 12b may be configured to rotate such that a complementary angle $\alpha_c$, between the elongate members 12a, 12b, as shown in FIG. 1B, can range from about 0° to 135° in each direction from a coaxial position, and more preferably from about 60° to 135° in each direction from a coaxial position. Once the elongate members 12a, 12b are in a desired position relative to one another, which is typically as a result of attaching the terminals ends 13, 15 of the elongate members 12a, 12b to an anchoring device, the fastening element 27 can be fully threaded into the bore 28c in the male connector 20b to cause the male connector 20b to engage the mating element 29, thereby preventing rotation of the second elongate member 12b relative to the first elongate member 12a.

Figure 2A:
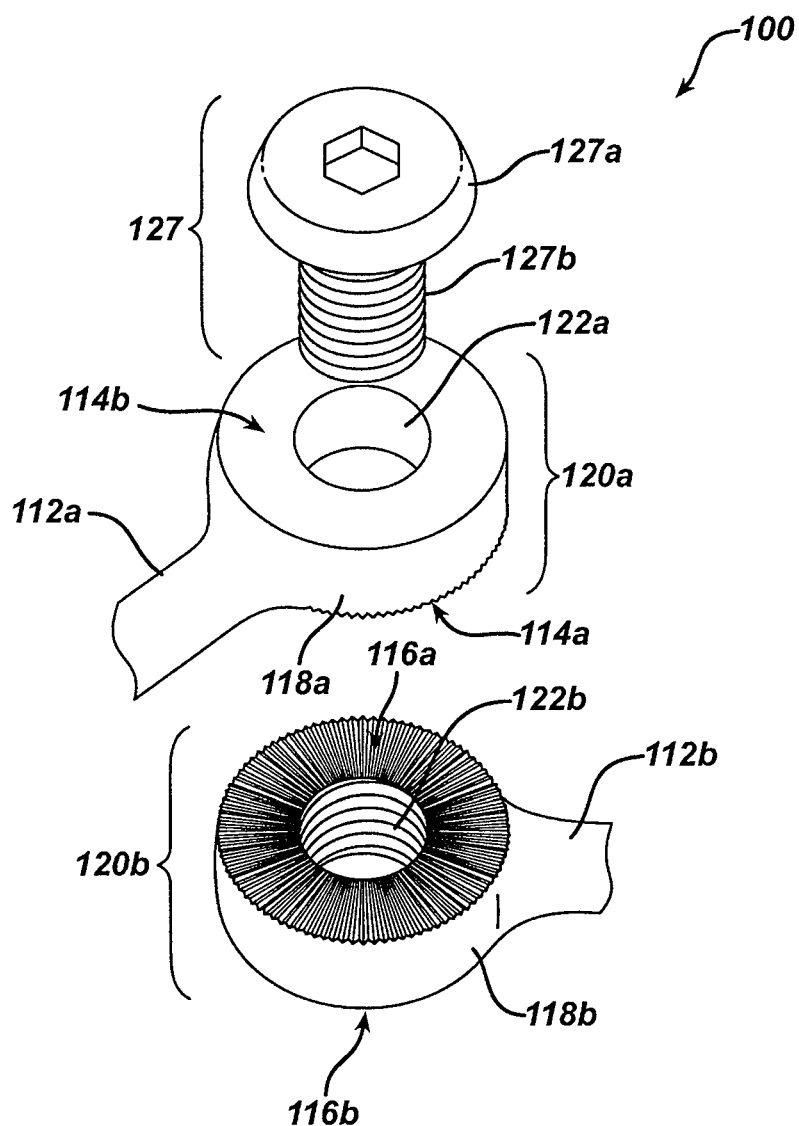
FIG. 2A is an exploded view of another embodiment of an adjustable-angle spinal fixation device according to the present invention having anti-rotation features formed thereon.
Figure 2B:
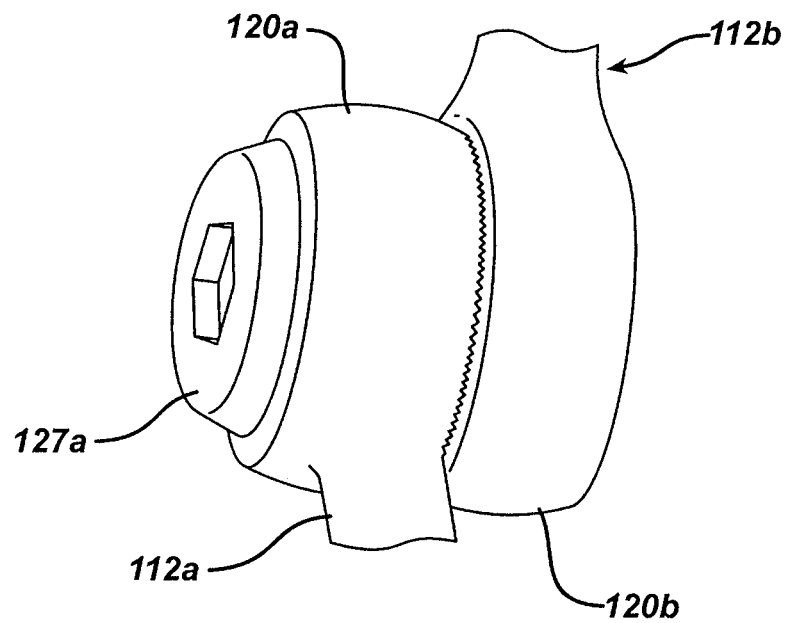
FIG. 2B is an enlarged side view of the adjustable-angle spinal fixation device shown in FIG. 2A in a locked position.

FIGS. 2A-2B illustrate another embodiment of a spinal fixation device 100 according to the present invention. In this embodiment, the spinal fixation device 100 includes a first elongate member 112a having a first connecting feature 120a formed thereon that is matable to a second connecting feature 120b formed on a second elongate member 112b. Each connecting feature 120a, 120b can have any shape and size, but in the illustrated embodiment the connecting features 120a, 120b have a substantially circular shape. Each connecting feature 120a, 120b also includes opposed inner and outer surfaces 114a, 114b, 116a, 116b, and the inner surface 114a, 116a of each connecting feature 120a, 120b is adapted to be positioned adjacent to one another. As a result, the elongate members 112a, 112b are offset from each other such that they are parallel to a plane of rotation. While not shown, one or both elongate members 112a, 112b can optionally be angled at any orientation relative to the plane of rotation, such that the elongate member(s) 112a, 112b intersects the plane of rotation.

Continuing to refer to FIGS. 2A-2B, the connecting features 120a, 120b also each include a central bore 122a, 122b extending through the inner and outer surfaces 114a, 114b, 116a, 116b thereof and adapted to receiving a locking mechanism 127. The locking mechanism 127, when disposed through the central bores 112a, 112b, allows the connectors 120a, 120b, and consequently the first and second elongate members 112a, 112b, to rotate there around. In an exemplary embodiment, each elongate member 112a, 112b can rotate 360° relative to one another. One skilled in the art will appreciate that certain applications may require a range of rotation of less than 360°, in which case a restriction, such as a mechanical stop, may be introduced to limit the range of rotation.

The locking mechanism 127 can have a variety of configurations, but in an exemplary embodiment, as shown, the locking mechanism 127 is a threaded member, e.g., a screw, that is similar to threaded member 27 shown in FIGS. 1A-1D. The central bore 122b in the first elongate member 120a can be configured to freely, rotatably receive the fastening element 127, and the central bore 122a in the second elongate member 120b can be threaded to mate with the threaded shank 127b of the fastening element 127. In use, when the fastening element 127 is in an unlocked position, it allows the first and second elongate members 112a, 112b to freely rotate relative to one another. Once properly positioned, the fastening element 127 can be fully threaded into the central bore 122b in the second elongate member 120b, as shown in FIG. 2B, to lock the connectors 120a, 120b in a fixed position relative to one another, thereby preventing rotation of the first and second elongate members 112a, 112b.

The configuration of the locking mechanism 127 on spinal fixation device 100 is particularly advantageous for use in lumbar or sacral-pelvic fixation. In particular, the fastening element 127 extends through the connecting features 120a, 120b in a direction that is substantially perpendicular to the plane of rotation of the elongate members 112a, 112b, thus allowing an insertion tool, such as a driver tool, to be used to thread the fastening element 127 into the connecting features 120a, 120b when the device 100 is implanted.

In a further embodiment, the inner surface 114a, 116a of each connector 120a, 120b can optionally include one or more anti-rotation features formed thereon. The anti-rotation features are effective to facilitate locking of the first and second elongate members 112a, 112b in a fixed position relative to one another. While various anti-rotation features can be used, each connector 120a, 120b can include gear teeth 118a, 118b formed thereon for engaging one another when the locking mechanism 127 is fully locked relative to the connectors 120a, 120b. In an exemplary embodiment, the gear teeth 118a, 118b have a size that allows angular positioning of the first and second elongate members 112a, 112b in 4° increments relative to one another, however any increment can be used.

Figure 3A:
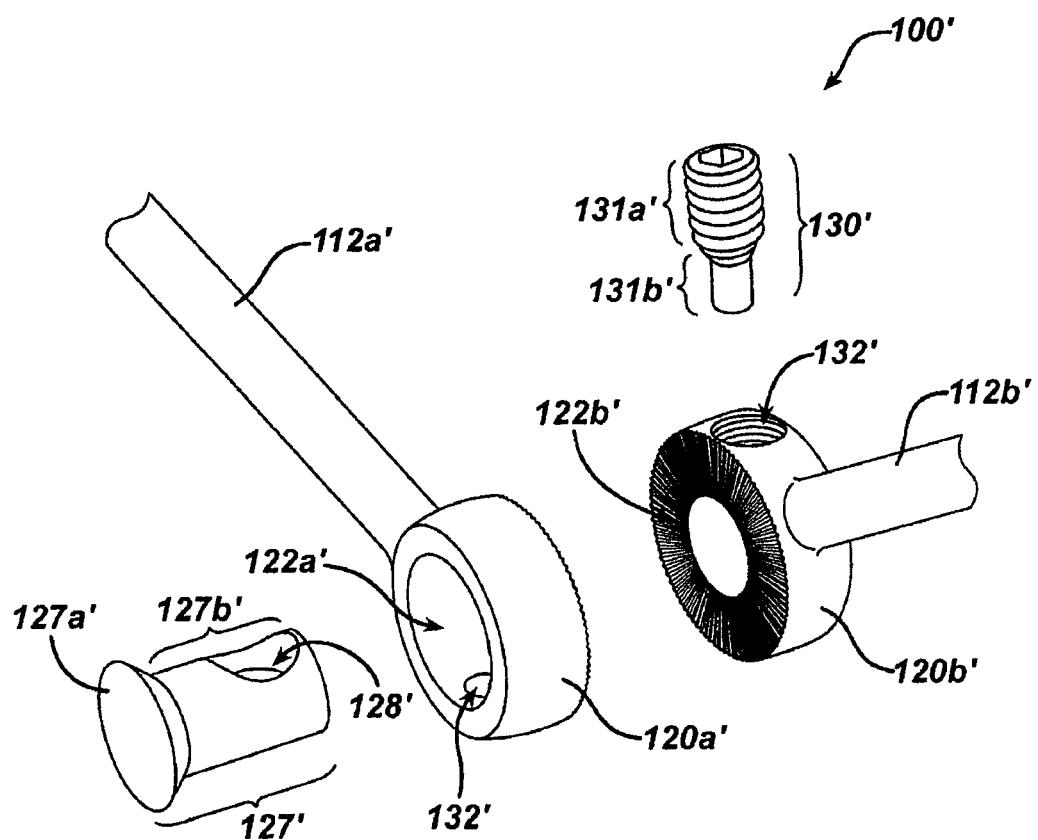
FIG. 3A is an exploded view of an adjustable-angle spinal fixation device having a pin member for receiving a fastening element according to yet another embodiment the present invention.
Figure 3B:
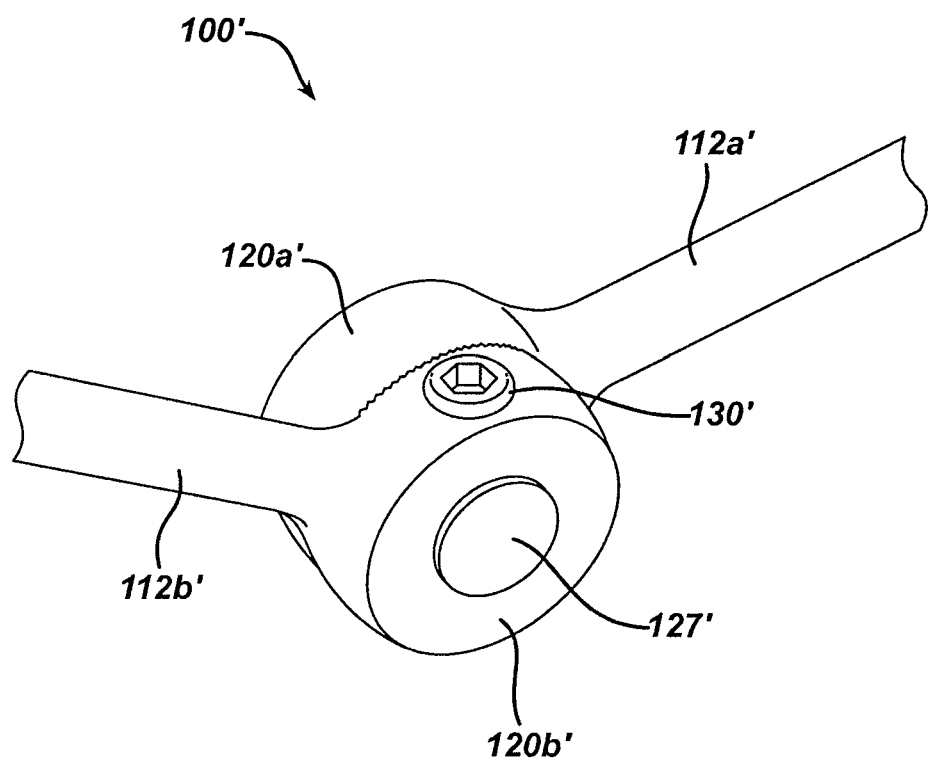
FIG. 3B is a perspective view of the adjustable-angle spinal fixation device shown in FIG. 3A in a locked position.

FIGS. 3A-3B illustrate yet another embodiment of a spinal fixation device 100' in accordance with the present invention. The device 100' is similar to the device 100 shown in FIGS. 2A-2B, and thus like reference numbers are used to refer to like parts. In this embodiment, the locking mechanism differs in that it includes a pin member 127', rather than a threaded member 127, that extends through the central bore 122a, 122b in each connector 120a, 120b. The locking mechanism also includes a fastening element 130 that is adapted to at least partially extend into the pin member 127' to lock the connectors 120a, 120b in a fixed position. The orientation of the fastening element 130' is particularly advantageous for use in occipital-cervical fixation since the fastening element 130' extends through the connecting feature 120b in a direction that is substantially parallel to the plane of rotation of the elongate members 112a, 112b.

The pin member 127' can have a variety of shapes and sizes, but in an exemplary embodiment it has head 127a' and a shank 127b' having a substantially cylindrical shape to allow the connector members 120a', 120b' to rotate there around. The head 127a' of the pin member 127' is configured to sit within a recess 132' formed within an opening of the central bore 122a' extending through the first connector 120a'. The shank 127b' of the pin member 127' is configured to extend through and sit within the bore 122a', 122b' in each connector 120a', 120b', and it includes a transverse bore 128' formed therein for receiving a portion of a fastening element 130'.

The fastening element 130' preferably includes a proximal threaded shank 131a' that is adapted to mate with a threaded receiving bore 132' formed in the second connector 120b', and a distal non-threaded shank 131b' that is adapted to extend into the transverse bore 128' formed in the pin member 127'. In use, the fastening element 130' can be partially threaded into the threaded bore 132' formed in the second connector 120b' to allow rotation of the first and second elongate members 112a', 112b' relative to one another. In this position, the non-threaded shank 131b' on the fastening element 130' extends into the transverse bore 128' in the pin member 127', and it preferably loosely engages the bore 128' to allow rotation between the first connector 120a' and the second connector 120b'. Further threading of the fastening element 130' into the threaded bore 132' will lock the angular position of the first and second elongate members 112a', 112b' relative to one another, as shown in FIG. 3B. While various techniques can be used to lock the first and second elongate members 112a', 112b' relative to one another, in one embodiment the this can be achieved by forming the transverse bore 128' in the pin member 127' at a location that is axially offset from the receiving bore 132' in the second connector 120b' when the pin member 127' is fully disposed therein. Thus, upon further rotation of the fastening element 130' into the receiving bore 132', the non-threaded shank 131b' causes the first connector 120a' to translate further toward the second connector 120b', thereby locking the connectors 120a', 120b' in a fixed position relative to one another. In this fixed position, the head of 127a' of the pin member 127' is preferably fully seated within the recess 132' formed in the bore 122a' of the first connector 120a'. In other embodiments, the transverse bore 128' and the non-threaded shank 131b' can contain features to translation and/or locking of the connectors 120a', 120b'. For example, a portion of the shank 131b', e.g., a distal end, and a portion of the transverse bore 128', e.g., an opening, can include conforming chamfers formed thereon.

As previously described with respect to connector 100 shown in FIGS. 2A-2B, an inner surface of each connector 120a', 120b' can include anti-rotation features formed therein, such as gear teeth or knurling to prevent rotation of the first and second elongate members 112a', 112b' relative to one another when the device 100' is in the locked configuration.

Figure 4A:
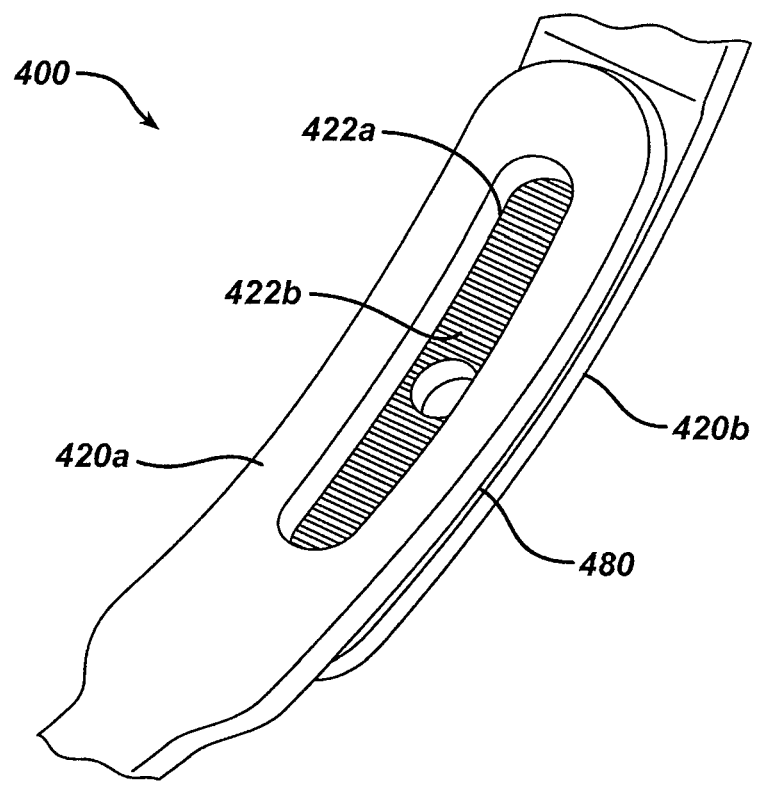
FIG. 4A is a perspective view of yet another embodiment of an adjustable-angle spinal fixation device according to the present invention having substantially curved complimentary matable connecting features.

FIGS. 4A-4B illustrate yet another embodiment of a spinal fixation device 400 in accordance with the present invention. In this embodiment, the connecting features 420a, 420b on the first and second elongate members 412a, 412b each have a substantially elongate, curved configuration such that they include complimentary matable surfaces 470, 472. One of the connecting features, e.g., the first connecting feature 420a, can include an elongate slot or opening 422a formed therein, and the other connecting feature, e.g., the second connecting feature 420b, can include a threaded bore 422b formed therein. The slot 422a and bore 422b are configured to receive a locking mechanism 430 that is effective to lock the first elongate member 420a in a fixed position relative to the second elongate member 420b. In an exemplary embodiment, the locking mechanism 430 includes threaded member 432 that can be disposed through the slot 422a in the first elongate member 420a, and that is matable with the threaded bore 422b in the second elongate member 420b.

In use, when the fastening element 432 is partially threaded into the threaded bore 422b, the first and second connectors 420a, 420b are slidably movable relative to one another, thereby adjusting the angle of the first and second elongate members 412a, 412b relative to one another. The radius of curvature can vary depending on the curvature of each connector 420a, 420b. Once properly positioned, the fastening element 432 can be fully threaded into the bore 422b to lock the elongate members 412a, 412b in a fixed position and at a fixed angle. A person skilled in the art will appreciate that the locking mechanism can be a rivet, pin, bolt or other fastening device known in the art.

In a further embodiment, the complimentary matable surfaces 470, 472 can include gear teeth formed thereon and adapted to prevent slipping or rotation when the locking mechanism 430 is in a locked position. While a variety of anti-slip features can be formed on the complimentary matable surfaces 470, 472, FIGS. 4A and 4B illustrate gear teeth (only gear teeth 480 on the second connecting feature 420b are shown) formed thereon.

Figure 5B:
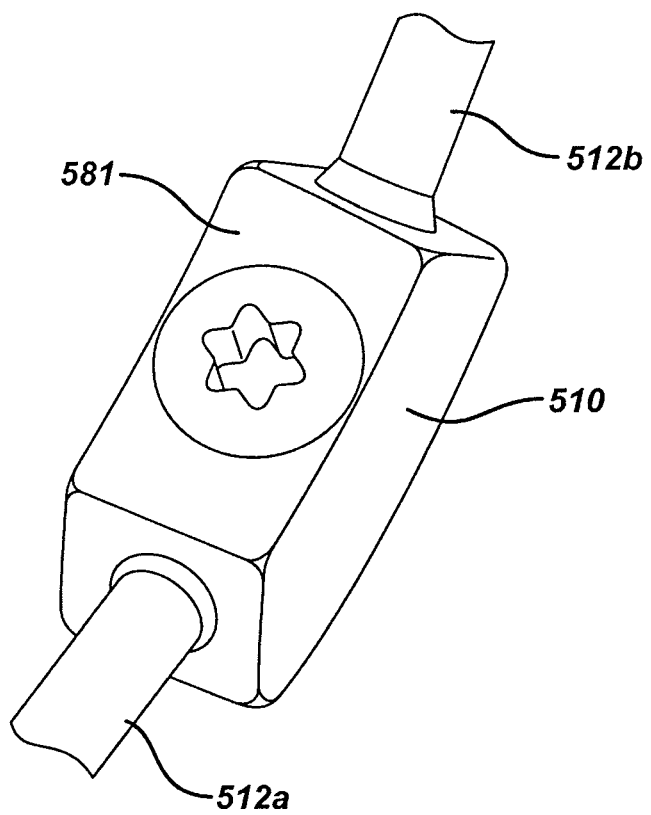
FIG. 5B is a top perspective view of the adjustable-angle spinal fixation device shown in FIG. 5B in a locked position.
Figure 5C:
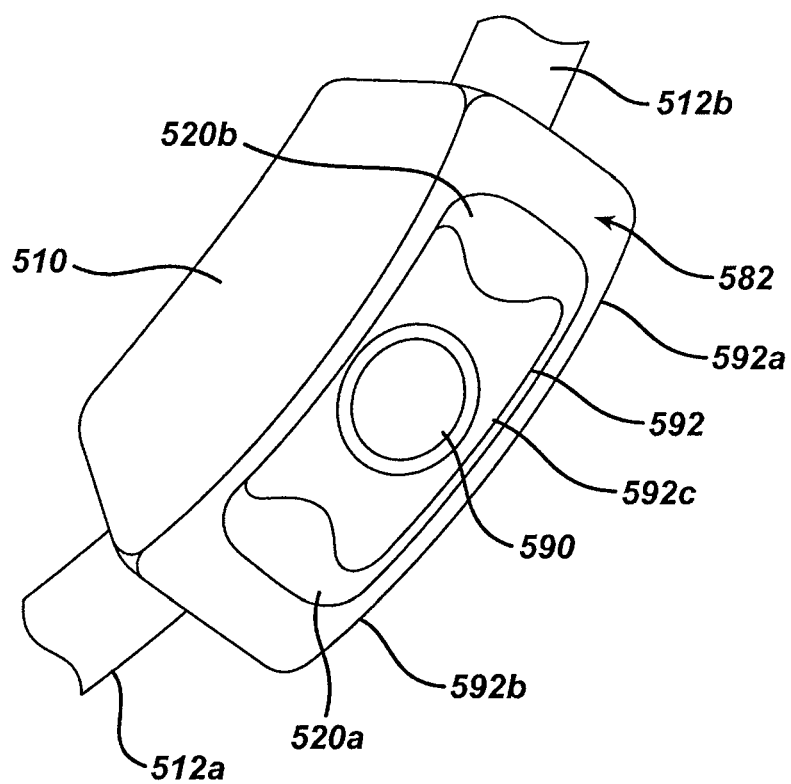
FIG. 5C is a bottom perspective view of the adjustable-angle spinal fixation element shown in FIG. 5A in a locked position.

FIG. 5A illustrates another exemplary embodiment of a spinal fixation device 500 according to the present invention. In general, the connecting feature 520a, 520b on each elongate member 512a, 512b is in the form of a protrusion that allows polyaxial movement of the elongate members 512a, 512b relative to the locking mechanism 530. While the shape of the protrusion 520a, 520b can vary, in the illustrated embodiment the each protrusion 520a, 520b has a generally bulbous shape. The locking mechanism 530 includes a housing 510 that is adapted to receive the protrusion 520a, 520b of each elongate member 512a, 512b such that the first and second elongate members 512a, 512b are substantially opposed to one another. Additionally, the locking mechanism 530 is adapted to lock the first and second elongate members 512a, 512b in a fixed position relative to one another, as shown in FIGS. 5B and 5C.

The housing 510 of the locking mechanism 530 can have a variety of shapes and sizes, but in the illustrate embodiment, the housing 510 has a substantially rectangular shape and it includes a central opening 585 formed therein and extending between opposed top and bottom surfaces 581, 582 thereof. Additionally, the housing 510 has at least two opposed side openings 583a, 583b, shown in FIG. 5A, extending from opposed first and second side surfaces 587', 588 thereof. Each elongate member 512a, 512b is positioned through the first and second opposed side openings 583a, 583b such that the bulbous protrusion 520a, 520b formed thereon is seated within the central opening 585 of the housing 510. Preferably, each of the first and second opposed side openings 583a, 583b in the housing 510 are sized to have a diameter $d_1$ that is smaller than a diameter $d_2$ of the bulbous protrusion 520a, 520b on each elongate member 512a, 512b to prevent the bulbous protrusions 520a, 520b from passing therethrough. The diameter $d_1$ of the opposed side openings 583a, 583b should, however, be larger than the diameter $d_r$ of each elongate member 512a, 512b to allow the elongate members 512a, 512b to extend therethrough and to rotate freely. In an exemplary embodiment, the side openings 583a, 583b allow the first and second elongate members 512a, 512b to rotate about 60° in all directions relative to the housing 510, and more preferably to rotate in the range of about 30° to 60°. As a result, the first and second elongate members 512a, 512b can form an angle in the range of about 0 to 120° relative to one another.

As previously stated, the locking mechanism 530 is also adapted to lock the elongate members 512a, 512b in a fixed position relative to one another. While various techniques can be used to lock the elongate members 512a, 512b in a fixed position, in the illustrated embodiment the locking mechanism 530 includes a fastening element 590, which can be a screw, rivet, bolt or other fastening device known in the art, that is adapted to mate to a receiver member 592. In the illustrated embodiment, the fastening member 590 is a threaded member having a threaded shank 590a that is adapted to extend through the central opening 585 to mate with the receiving member 592, and a head 590b that is adapted to rest against or sit within a portion of the central opening 585 formed in the top surface 581 of the housing.

The receiver member 592 is preferably positioned within a portion of the central opening 585 that is adjacent to the bottom surface 582 of the housing 510, and it has a shape that is effective to lock the bulbous protrusion 520a, 520b on each elongate member 512a, 512b in a fixed position within the central opening 585 when the fastening element 590 is mated thereto. In particular, the receiving member 592 can have a substantially rectangular shape, as shown in FIG. 5C, and it can include opposed concave side surfaces 592a, 592b formed thereon. In use, the fastening element 590 can be threaded into a corresponding threaded bore 592c extending through the receiving element 592 to engage the receiving element 592 and pull it into the central bore 585 formed in the housing 510. As the receiving element 592 moves into the central bore 585, the opposed side surfaces 592a, 592b abut against the bulbous protrusion 520a, 520b on each elongate member 512a, 512b to lock the protrusions 520a, 520b in a fixed position relative to the housing 510.

A person skilled in the art will appreciate that the configuration of the protrusion 520a, 520b on each elongate member 512a, 512b and the receiving element 592 can vary. For example, each connecting features 520a, 520b can have a substantially concave recess formed therein, and the receiving element 592 can include convex side surfaces formed thereon for engaging the connecting features 520a, 520b.

It is possible that some applications will require angular adjustability of only one of the elongate members. Accordingly, in each of the various embodiments of the present invention, one of the elongate members can be angularly adjustable and the other elongate member can maintained in a fixed position.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A spinal fixation system, comprising:
   a first elongate member having a first connector at a terminal end thereof;
   a second elongate member having a second connector at a terminal end thereof that includes spaced apart protrusions that are configured to receive a portion of the first connector therebetween;
   a pin configured to extend through the first connector and the second connector such that a longitudinal axis of the pin is transverse to a longitudinal axis of at least one of the first and second elongate members;
   a fastening element configured to thread into a bore formed in the second connector;
   wherein translation of the fastening element into the bore changes the system from a first configuration in which the first and second elongate members can rotate relative to one another about the longitudinal axis of the pin to a second configuration in which the first and second elongate members are locked relative to one another.

2. The system of claim 1, wherein the fastening element extends through the second connector in a direction that is substantially parallel to a plane of rotation of the first and second elongate members that is perpendicular to the longitudinal axis of the pin.

3. The system of claim 1, wherein the first connector is integrally formed with the first elongate member and the second connector is integrally formed with the second elongate member.

4. The system of claim 1, wherein the first and second elongate members are biocompatible, internally implantable spinal rods.

5. The system of claim 1, further comprising a plurality of spinal anchors adapted to mate to at least one of the first and second elongate members.

6. The system of claim 5, wherein the plurality of spinal anchors includes at least one of a hook, a screw, a bolt, a plate, and a wire.

7. The system of claim 1, wherein at least one of the first and second elongate members is a spinal fixation plate.

8. The system of claim 1, wherein at least one of the first and second elongate members is a substantially cylindrical spinal rod.

9. The system of claim 1, wherein the fastening element contacts the pin.

10. The system of claim 1, wherein the fastening element extends through a recess formed in the pin.

11. A spinal fixation system, comprising:
    a first elongate member;
    a second elongate member;
    a locking mechanism configured to selectively couple the first and second elongate members in a first configuration in which the first and second elongate members can move relative to one another, and a second configuration in which relative movement between the first and second elongate members is restricted, the locking mechanism including:
      a connector coupled to the first elongate member and the second elongate member; and
      a threaded mating element that extends through a bore of the first connector, the mating element having a central axis that is transverse to a longitudinal axis of at least one of the first and second elongate members and about which at least one of the first and second elongate members moves, the threaded mating element being disposed a distance from the second elongate member;
    wherein advancement of the mating element into the bore restricts relative movement between the first and second elongate members.

12. The system of claim 11, wherein the connector is integrally formed with one of the first or second elongate members.

13. The system of claim 12, wherein the connector is formed on a terminal end of one of the first or second elongate members.

14. The system of claim 11, wherein the first elongate member and the second elongate member are pivotally connected.

15. The system of claim 11, wherein at least one of the first and second elongate members is a substantially cylindrical spinal rod.

16. The system of claim 11, wherein at least one of the first and second elongate members is a spinal fixation plate.

17. The system of claim 11, further comprising a plurality of spinal anchors adapted to mate to at least one of the first and second elongate members.

18. The system of claim 11, wherein the connector is configured to receive a portion of the second elongate member between spaced apart protrusions thereof.

19. The system of claim 11, wherein the connector has an anti-rotation feature formed thereon.

20. The system of claim 11, wherein the connector is coupled to the first elongate member and the second elongate member includes a second connector coupled to a terminal end thereof.

21. The system of claim 20, wherein the threaded mating element also extends through a bore formed in the second connector.

22. The system of claim 20, wherein each of the first and second connectors include anti-rotations featured formed thereon that are configured to interface with one another as the mating element is advanced into the bore.

* * * * *